United States Patent [19]
Abbate

[11] Patent Number: 4,836,192
[45] Date of Patent: Jun. 6, 1989

[54] VACUUM GENERATOR FOR STIMULATING THE SCALP

[75] Inventor: Mariarosa Abbate, Via Camperio, 8-20052 Monza, Italy

[73] Assignees: Mariarosa Abbate; Ciulio Corti, both of Monza, Italy

[21] Appl. No.: 225,281

[22] Filed: Jul. 28, 1988

Related U.S. Application Data

[63] Continuation-in-part of Ser. No. 883,069, Jul. 8, 1986, abandoned, and a continuation-in-part of Ser. No. 145,652, Jan. 7, 1988, abandoned, said Ser. No. 145,652, is a continuation of Ser. No. 815,800, Jan. 6, 1986, abandoned, which is a continuation of Ser. No. 531,504, Sep. 12, 1983, abandoned.

[30] Foreign Application Priority Data

Sep. 20, 1982 [IT] Italy ................................ 2338 A/82
Jul. 17, 1985 [IT] Italy ................................ 22525 B/85

[51] Int. Cl.⁴ ........................ A61H 9/00; A61H 1/00
[52] U.S. Cl. ........................................ 128/38; 128/40
[58] Field of Search ...................... 128/38, 32, 40, 44, 128/43, 24 R, 420 R, 380

[56] References Cited

U.S. PATENT DOCUMENTS

| | | | |
|---|---|---|---|
| 809,360 | 1/1906 | Dible | 128/38 |
| 1,704,960 | 3/1929 | Ackerman | 128/38 |
| 1,744,443 | 1/1930 | Businger | 128/38 |
| 2,232,218 | 2/1941 | Dotty | 128/38 |
| 2,626,601 | 1/1953 | Riley | 128/38 |
| 2,655,145 | 10/1953 | Heger | 128/38 |
| 2,972,346 | 2/1961 | Eddings | 128/38 |
| 3,516,411 | 6/1970 | Adler | 128/38 |
| 3,841,322 | 10/1974 | Spelio | 128/40 |
| 4,003,373 | 1/1977 | Spelio | 128/40 |
| 4,296,743 | 10/1981 | Lasley | 128/30 |

*Primary Examiner*—Edgar S. Burr
*Assistant Examiner*—Huong Q. Pham
*Attorney, Agent, or Firm*—Bucknam and Archer

[57] ABSTRACT

The stimulation of scalp and falling of hair is stopped and the hair growth is promoted by applying to the scalp first a sliding, zig-zag suction followed by a pulsating, that is, variable, suction, applied at right angles to the skin to activate the circulation of blood and lymph and the nourishment of the hair bulbs. The suction actions may be combined with a treatment with warm solution containing vasodilators, stimulants and fixatives of the blood and lymph drawn up and with infrared and ultraviolet ray treatments.

14 Claims, 7 Drawing Sheets

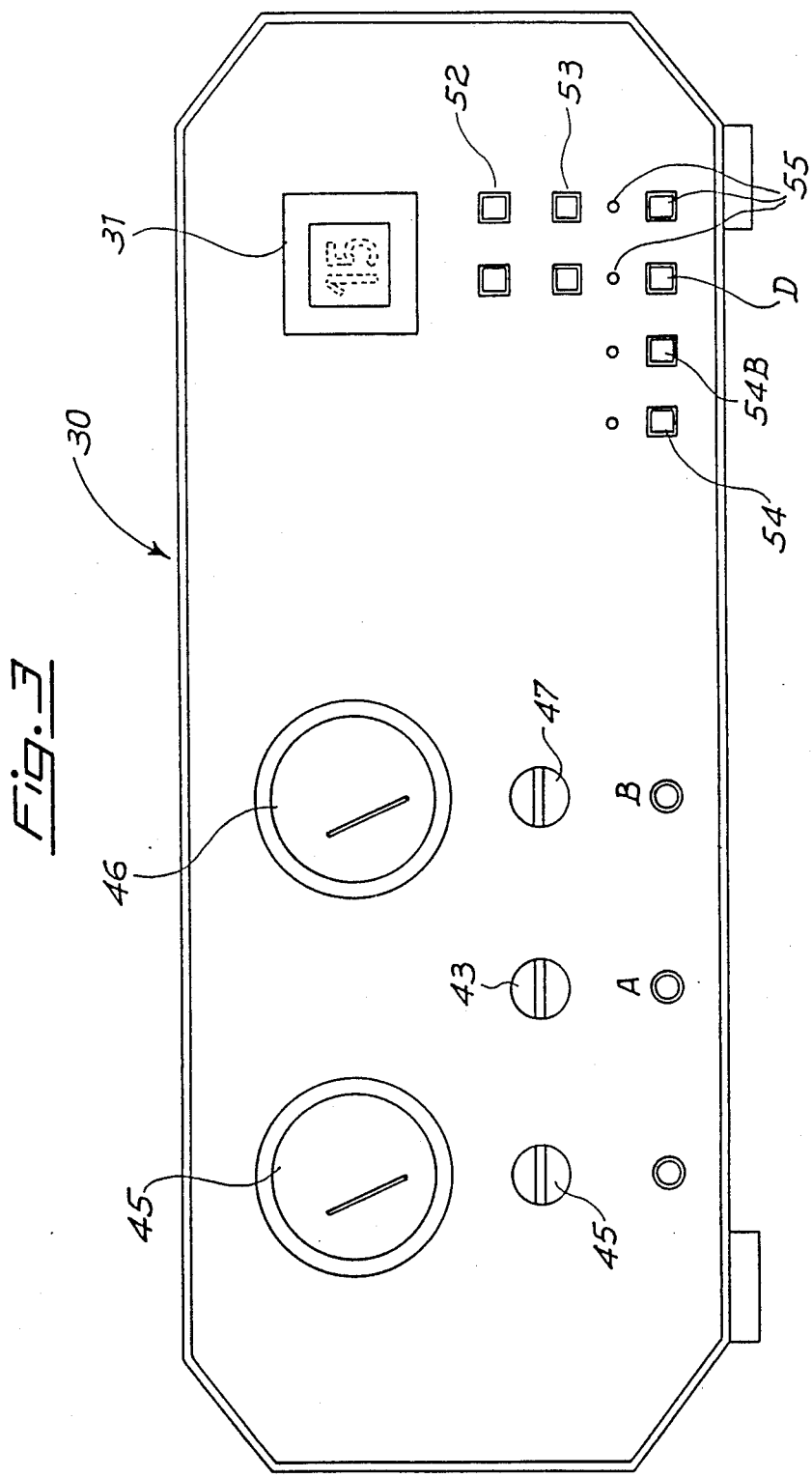

X

X

VACUUM GENERATOR FOR STIMULATING THE SCALP

This application is a continuation-in-part of U.S. Ser. No. 883,069 filed July 8, 1986 now abandoned and U.S. Pat. No. 145,652 filed Jan. 7, 1988 will be abandoned on 1/10/1989. U.S. Ser. No. 145,652 was a continuation of U.S. Pat. No. 815,800 filed Jan. 6, 1986, now abandoned which was a continuation of U.S. Pat. No. 531,504 filed Sept. 12, 1983 now abandoned.

This invention refers to a method and device for increasing the circulation of blood and lymph and the nourishment of the hair bulbs on the scalp.

In particular, this invention refers to the use of a vacuum generator to increase the circulation of the blood and lymph and the nourishment of the hair bulbs, particularly suitable for stimulating the scalp, stopping the falling of hair and promoting hair growth.

It is known that the human scalp has an average of 1,000 hair follicles per square inch. At the bottom of the follicle which is a pocket, is a finger-like projection called the "papilla". The hair bulb forms a socket for the papilla. Within the hair papilla is a blood supply which permits the growth and generation of the hair.

The hair follicle is supported in a layer of tissue called the reticular layer. The outer layer of the skin is the epidermis. The undersurface of the reticular layer, below the hair follicle, rests on a layer of fatty tissue termed the "adipose tissue". The scalp moves upon the skull. In a normal individual the human head sheds 50-80 hairs per day. As each hair sheds, it separates from the papilla and the root gradually works upwardly through the follicle until it falls from the scalp. While the hair is moving upwardly through the follicle, the papilla gives life to a new hair which replace the one being lost. As described in Arthur Rook-Rodney Dawber-Malattie dei capelli e del cuoio capelluto-LE-Capozzi Editore, pages 10-13, the stages of the natural biological cycle of hair are:

anagen (productive phase of the hair cycle in a follicle) the average duration of which is about 2-5 years;

catagen (transition phase): 2 weeks;

telogen (quiescent stage): 3-4 months. This stage lasts until the hair is shed and anagen again.

In the anagen stage, hair grows about one-half inch per month. The hair has a life cycle of 2 to 6 years and as the hair sheds, the papilla gives life to a new hair. At about 16-18 years of age for men, later for women, the transition stage (catagen) begins. The galea, interposed between the adipose tissue and the areolar tissue is a resilient layer which permits the scalp to move with respect to the skull. During the transition stage, the galea loses its resiliency, begins to thicken, expands outwardly and exerts pressure upon the adipose tissue. The pressure from the expanding galea is exerted upon the blood vessels and the lower end of the follicle. The result is that the papilla receives a decreased supply of oxygen and blood. The pressure also foreshortens the follicle. In the telogen stage, which is the terminal stage, the galea has expanded and has lost substantially all resiliency. The pressure decreases almost completely the blood flow to the papilla. The hair follicle because of the pressure shortens to approximately one-half its original length and without nutrient flow into the papilla, ceases to function. The hair follicle is not dead, but reaches the telogen or resting stage. In the telogen stage, the scalp cannot generally be displaced more than one-eighth inch upon the skull.

One of the main causes for falling hair is the reduced circulation of blood and lymph caused by the reduced size of the epithelial bed. In fact, the insufficient nourishment received by the hair, due to a decreased blood and lymph circulation in the epithelial bed in which it is inserted, as well as insufficient oxygen supply, causes the hair loss.

Also, the stagnation of waste matters arising from tissular breakdown and the accumulation of fats due to hypersecretion and poor elimination prevent the regular access of oxygen to the same tissues. In these conditions, the normal conditions for the hair growth are lacking, the hair falls and a difficult or impossible regrowth of a new hair occur.

U.S. Pat. No. 4,428,368 to Torii discloses a massage pulsating device which helps to promote the health and the beauty of the body. According to this reference, air suction and pressure are alternately applied on the surface of the body to activate the working of the subcutaneous tissue and to produce blood circulation by alternately causing the contraction and explansion in the subcutaneous muscular and cellular tissue, and to exchange the fats and other waste matters with fresh secretion. The massage device of this reference, however, could not be used on the scalp and would cause irritation of the scalp skin.

U.S. Pat. No. 3,841,322 to Spelio describes a process and apparatus for stimulating facial and neck tissue by improving lymphatic and venous circulation and improving arterial blood flow and reestablishing capillary permeability. The process consists of rhythmic mechanical manipulative action, i.e. application of cyclic contraction and relaxation to the facial and neck area, by means of frusto-conical cup connected to a variable pulsating vacuum pneumatic device. Spelio, U.S. Pat. No. 4,003,373 regulates the unit to give 130-190 revolutions per minute.

SUMMARY OF THE INVENTION

An object of the present invention is to provide a method and a device for stimulating the scalp, stopping the fall of hair and promoting the hair growth.

It is another object of this invention to provide a method and a device which allow an increase in the blood circulation and the lymph in the scalp and the nourishment of the hair bulbs.

It has now been found that the above objects are achieved by a method which comprises the treatment of the scalp first with a sliding, zig-zag suction and then with localized, prolonged pulsating suction and decompression actions, applied at right angles to the skin, so as to cause a temporary dilatation of the capillaries and the vessels facilitate the flow of the blood and lymph and stimulate the circulation from the inside towards the outside and from the outside towards the inside.

The above suction actions are produced by two different suction means: the sliding suction and decompression action is obtained by frusto-conical suction means, running over the skin of the scalp; and the localized, prolonged and pulsating suction and decompression action is obtained by cup-shaped suction means, fixed to every area of the scalp.

Prior to and after the application of the two suction actions, the skin may be treated with a warm solution applied to the scalp including vasodilators, stimulants, fixatives of the blood and the lymph.

Before and after each treatment cycle, the follicular cycle dynamics of the hair of the patient is examined to determine the percentage of the hair in the anagen stage, in the catagen stage and in the telogen stage to establish the successive treatment cycle and conditions.

The studies of the follicular cycle dynamics are based on the dermatological tricological analysis, generally called trichogram (see Arthur Rook-Rodney Dawber-Malattie dei capelli e del cuoio capelluto LE-Capozzi Editore pages 14–17) which consists in comparing the hairs in the anagen and telogen stage by examination of pulled hair by microscope. This technique gives remarkable results provided that at least 20 hairs, and preferably 50 hairs are examined. Hair is washed 2 to 3 days before test, because washing eliminates hair in telogen stage. It should be noted that the hair root is much less damaged by quickly pulling rather than by a slow traction.

In normal subjects the percentage of hair is: man: 83% in the anagen stage; 2.9% in catagen stage and 15% in telogen stage. Woman: 85% in the anagen stage; 2.1% in catagen stage and 11% in telogen stage. The above technique is necessary to evaluate the three stages (anagen, catagen, telogen) because it allows to check if the telogen stage is altered, with an acceleration and therefore an increase of the number of hair in telogen stage.

The object of the sliding suction action followed by the prolonged suction, alternating with different values and therefore "pulsating", suction and decompression actions is that of creating a stimulation of the capillary tissue as high and as differentiated as possible. The stimulations, created by the suction actions of the suction cups, work with forces substantially at right angles to the skin and from the inside towards the outside and the outside towards the inside, drawing the blood and the lymph from the areas of greatest depth and stimulating the cellular metabolism and the expulsion of waste matters and stagnant water.

The sliding suction action is achieved by using frusto-conical suction cups, with a small diameter capable of creating a concentrated suction actions as they are transferred from one area of the scalp to the other, in a zig-zag fashion.

The vacuum generator can be of any well-known type and provided with connections for suction cups of various types for the suction actions required. The vacuum generator is provided with one or more regulators for the degree of vacuum and a timer to automatically determine the duration of each application.

The device then allows in the second stage for the cyclical variation of the degree of vacuum, in such a way that phases of greater vacuum alternate with phases of moderate vacuum and viceversa, as it also allows the variation of the time of each application. Devices for the programming and automatic regulation of the intensity, of the periods and the cycles can also be used.

According to the preferred embodiment of the present invention, the effects of the suction action are increased by a prior treatment of the epithelial cells with a warm solution applied to the scalp. The warm solution may include vaso-dilators, such as alcohol and sulphur, stimulants, such as nettle and burdock, "fixatives" of the blood and the lymph such as rosemary.

The stimulation of the hair bulbs by suction action, may be optionally followed by a treatment with infrared rays and with ultraviolet rays.

The crux of the present invention resides in using the sequence:

(a) a suction action, for a period of roughly 1 hour, with a vacuum generator provided with frusto-conical suction cups, sliding for roughly five minutes over all areas of the scalp in a zig-zag fashion;

(b) a suction action, for a period of roughly 1 hour, with a vacuum generator provided with wide diameter suction cups, fixed to every area of the scalp for roughly 10 minutes and with a "pulsating" and cyclic suction action that is alternating from high to low vacuum; carried out one after the other in the same sitting.

The treatment first with sliding suction and then with pulsating and cyclic suction is repeated once a week.

A warm solution containing vasodilators, stimulants and fixatives of the blood and the lymph is preferably applied prior to step (a) and/or after the step (b).

Infrared radiation for a period of about 10–15 minutes associated with the treatment with the warm solution described above, and ultraviolet radiation for a period of roughly 10 minutes may also be optionally used. The treatment with the warm solution is preferred in order to improve the suction actions and to give a refreshing and pleasant feeling to the patient.

In particular, the sliding suction cups used in step (a) must apply a vacuum sufficient to maintain a nearly tight contact on the skin, so that they can remain sucking, but at the same time they can slide on the scalp. For this purpose, a suitable shape in such that the end portion is formed by rounded off edges having a thickness high enough to bear the sealing load, by letting expand the inner air, but remaining easily slidable without irritating the outer epithelium, and massaging it upon sliding, while the inner vacuum sucks the blood and lymphatic fluids from the deeper layers.

A particularly suitable shape of sliding suction means is of frusto-conical type, having small diameter, preferably from 10 to 20 mm, with walls of about 2–4 mm in thickness, and with rounded edges, having a diameter of the same order of magnitude as of the walls. These sliding suction means are made of material which is neither heat-conductive, nor subject to be damaged and should not absorb moisture and fats. A polyamide is preferably used.

The stationary suction means used in step (b) are intended to operate under stationary positioning with pulsating suction, viz., with vacuum value alternately varying between maximum and minimum values and have a much greater surface area with a diameter of about 35–50 mm, so that when the vacuum varies between 0.1 and 0.75 $kg/cm^2$, the suckers are kept under a thrust in the order of 2–15 kg, for about 10 minutes. Under loads of such values, they must remain for long time on an epithelial area without wearing off the skin at their edges, and for this purpose, a large-radius profiling of the edges and the adoption of a not irritating, not heat-conductive material are needed, due also to the reduced depth of the epithelial layer. Vacuum-generating appliances of known type, already applied for other treatments and equipped with joints for suckers and vacuum control means, can be used for the treatment of the thin epithelial layer which constitutes the scalp. It should be noted, however, that the appliance should allow the vacuum to be very finely graduated, so to promptly match the sensibility of the patient and operating condition for a well determined patient to be constantly preserved with time, must be used.

For this purpose, the present invention provides a particular model of appliance, which allows the steps of the cycle to be controlled and which permits to follow the progress by electronic moderators, in particular by a microprocessor.

BRIEF DESCRIPTION OF THE DRAWINGS

The structural and functional characteristics of the device, which is an object of the present invention, may be better understood from the following detailed disclosure, wherein reference is made to the attached drawings, which represent a preferred, exemplifying and non-limitative embodiment of the present invention and wherein:

FIG. 3 represents a front schematic view of a central panelboard with the controls for the optical display of the individual steps and with the vacuum level measuring instruments;

DESCRIPTION OF THE PREFERRED EMBODIMENTS

Figure 1:
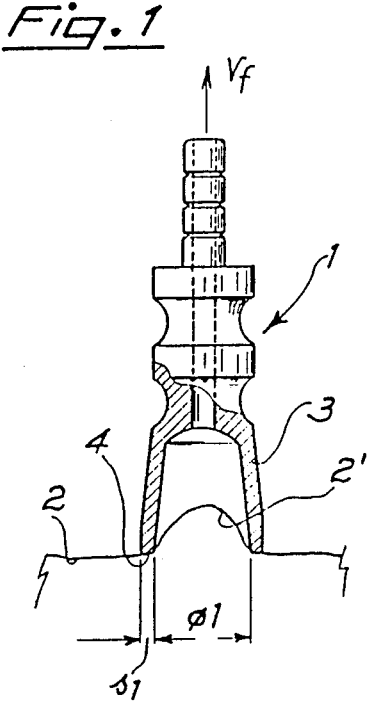
FIG. 1 represents a schematic view of the calibrated profile and of the structure of the sliding frusto-conical suction means.

In FIG. 1 the sliding suction means 1 is shown, of small diameter (from 10 to 20 mm, preferably 15 mm), which is placed on the skin 2 of the patient with its walls 3 of thickness "$s_1$", and having its top edges with rounded profile, with a diameter equal to the same thickness "$s_2$", preferably 2 mm.

The suction means is constituted by a not heat-conductive, semi-rigid material, preferably nylon 6 or nylon 66. It is obtained by moulding or by mechanical machining from rod, and is perfectly polished. When the stationary partial vacuum $V_f$, preferably of 0.3–0.75 kg/cm$^2$ is applied, the skin 2 is deformed to 2', and comes to rest against the rounded edges, creating a fairly tight seal, without blocking the underlying capillaries, and allowing a manual side pressure to slowly slide the sucker throughout the portion of area of 2–6 cm to be treated with the vacuum not being interrupted. The treatment with the sliding suction means 1 is repeated for each portion of the scalp skin 2.

Figure 2B:
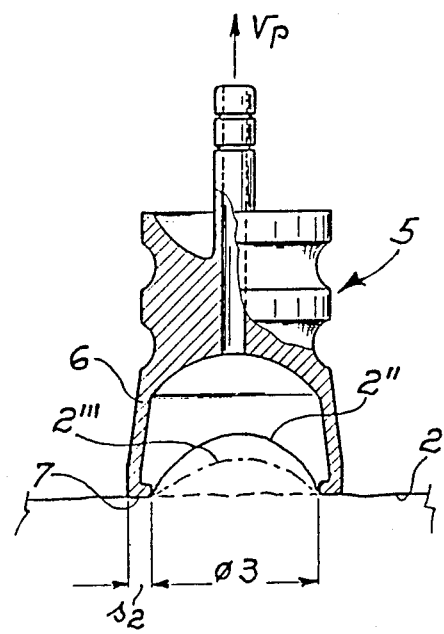
FIG. 2B represents the same view of FIG. 2A of a stationary suction means having a reduced cross-sectional area.
Figure 2A:
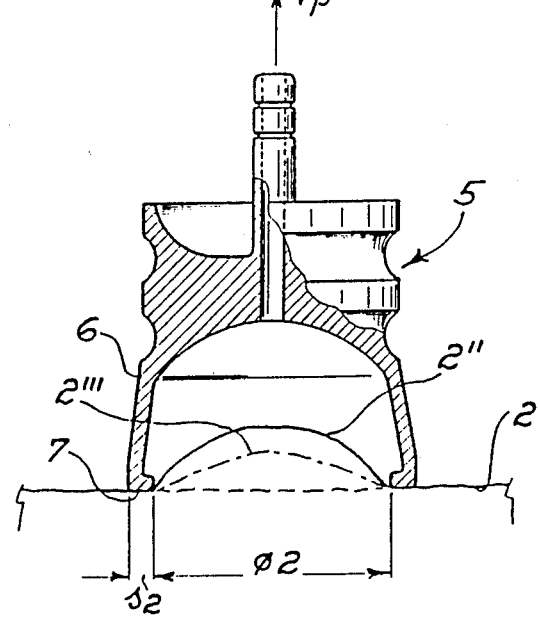
FIG. 2A represents a schematic view of the calibrated profile of the stationary suction means applying the pulsating suction pressure.

In FIG. 2A, the stationary suction means 5 applying the pulsating partial vacuum is shown; it is of larger diameter than suction means 1 (from 25 to 50 mm, preferably of 40 mm), and is lying on the skin 2, already previously treated by the sliding suction means 1, through the wall 6 ending with inwardly curved rounded edge 7 of thickness "$s_2$", and with curvature diameters equal to the same thickness, and preferably of 4 mm. The suction means 5, in this case too, made from semirigid and not heat-conductive material, preferably from nylon 6 or 66, which does not irritate the skin, and can produce a tight seal without intermediate gaskets even under very low values of vacuum $V_P$ which can alternatively vary between vacuum of from 0.1 to 0.75 kg/cm$^2$, so maintaining a thrust ranging from 2 to 15 kg. Under such a vacuum variable with selected frequency, the skin 2 is cyclically deformed between extreme positions 2" and 2''', which create a continuous perpendicular flux and reflux between the outmost and the deepest epithelial layers, whilst the magnitude of the deformed area induces also transversal equalizer fluxes.

The small diameter sliding suction means 1 is provided with a rounded smooth edge for the contact with the scalp surface. The stationary suction means 5 is provided with an inwardly curved peripheral flange 7 for assuring the stability of the suction means on the skin in the vacuum stage and for avoiding compressions on the skin which prevent the blood afflux from the deepest derm to the surface derm. The outwardly curved flanges would not be suitable for this purpose. Suction means 1 and 5 are connected by means of the usual flexible hoses with screw, plug or bayonet joint to the central panel board of the appliance, mounted with the container, wherein the vacuum pump and the actuating pneumatic devices, as well as the electrical and electronic actuation devices are housed, being inspectable.

Figure 4:
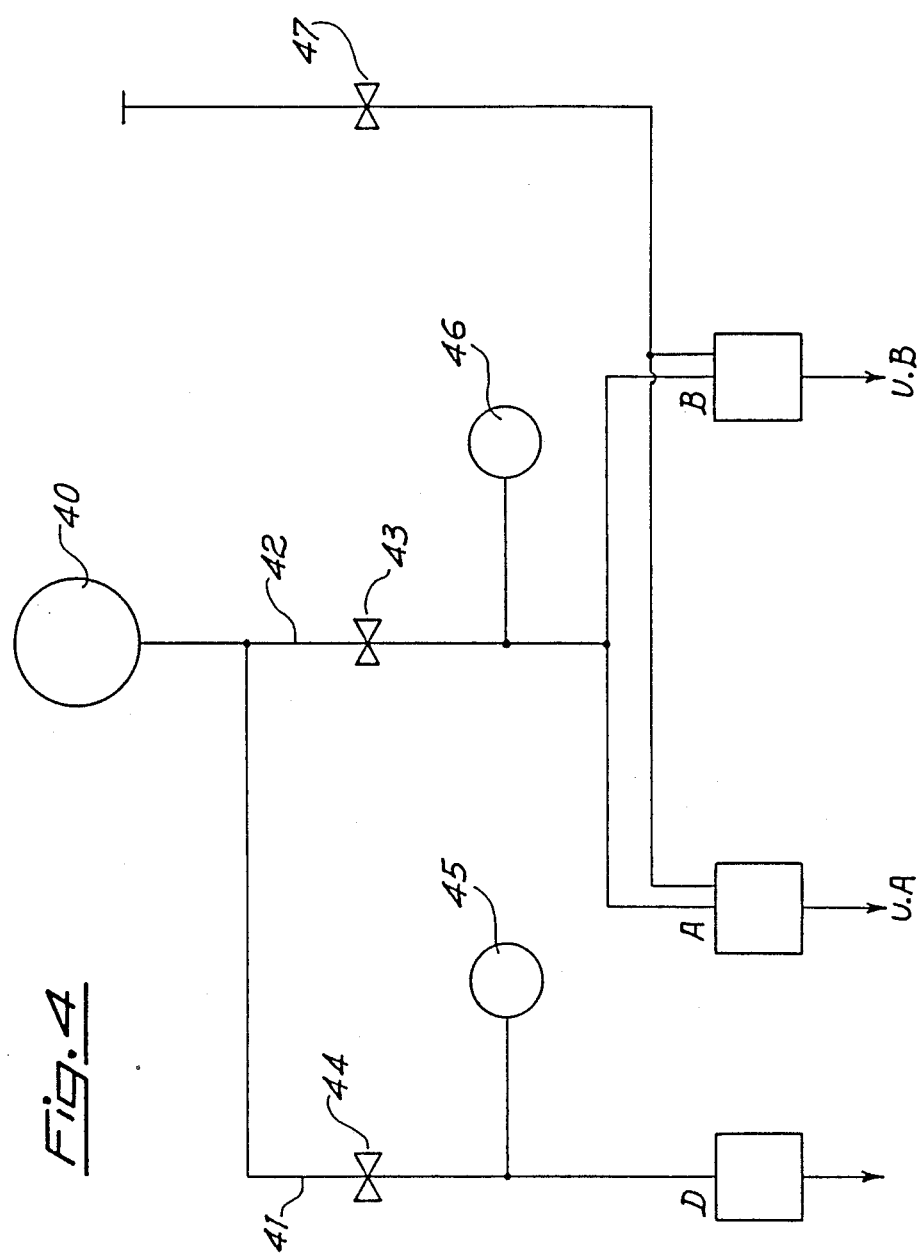
FIG. 4 represents a diagram of a pneumatic system for performing the individual steps.

In particular, and referring to FIGS. 3 and 4, from the vacuum pump 40 two pneumatic circuits 41 and 42 branch off, respectively for the sliding suction and the pulsating suction, each circuit being provided with micrometric adjustment means 43 and 44 respectively, and with vacuum gages 45 and 46 respectively.

The circuit of the pulsating suction is connected also to the pressure regulator 47, which allows the cyclic partial inlet of air to reduce the vacuum level. The regulators operate under control by an electronic circuit, which define very finely the values, and guarantees their exact reproducibility with time.

The function of the sliding massage is always performed by one single suction means D of type 1 of FIG. 1, whilst the function of suction locally stable and with value cyclically variable between minimum and a maximum value can be performed by two suction means, by the joints A, B being multiple, so that at the same time either a plurality of suction means of the same shape can be operating, or some suction means having a diameter reduced to about 25 mm (see FIG. 2B) can be used, to match particular profiles of patient's head.

Figure 5:
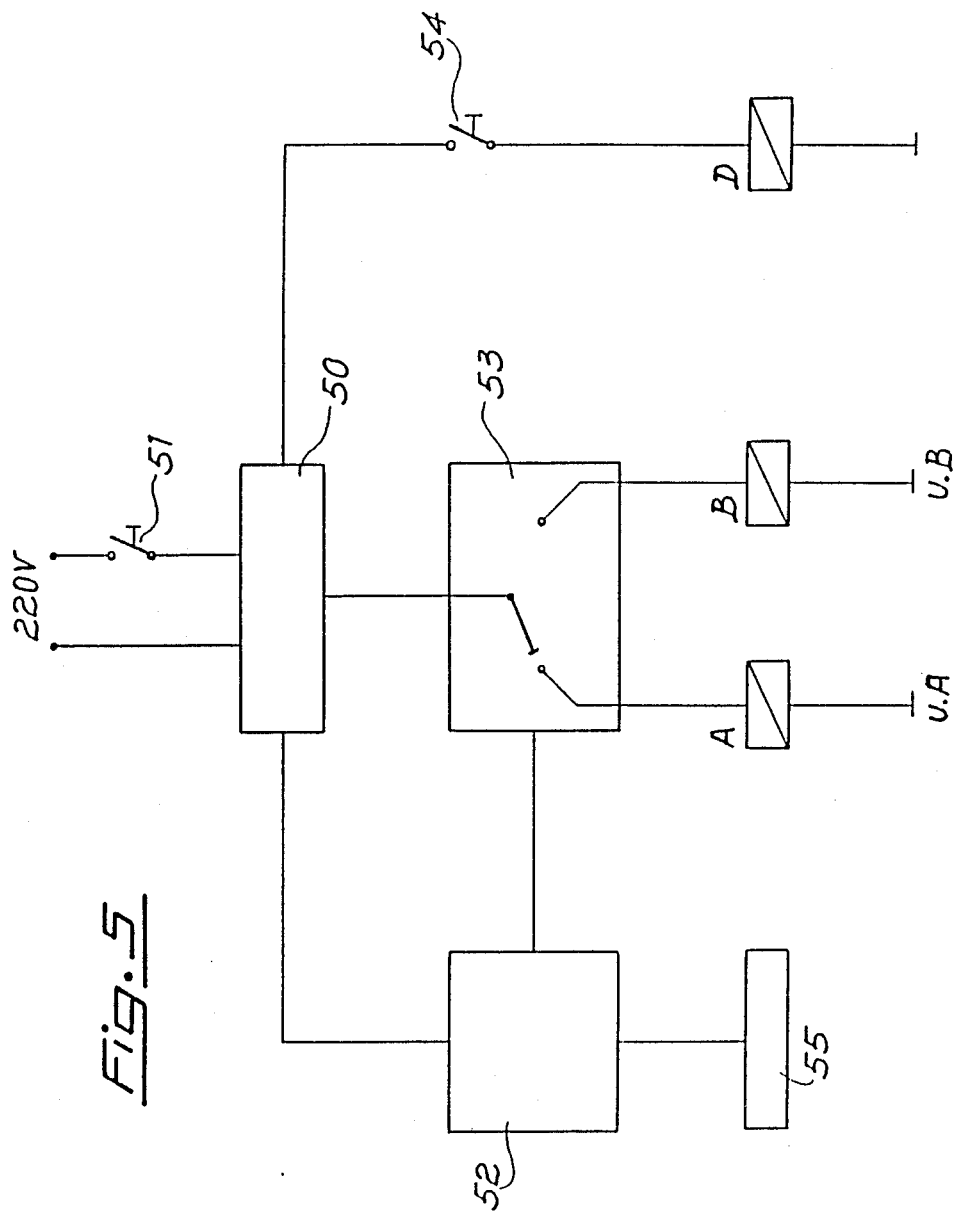
FIG. 5 represents the wiring diagram which allows the individual steps of the pneumatic apparatus to be actuated, displayed and timed.

In the writing diagram of FIG. 5, the electric or electronic components from normal industrial production are shown, which actuate and control the pneumatic device throughout its various operating steps. A power feeder 50, connected to the mains (generally at 220 V 50 Hz), by switching on switch 51 feeds both the motor of the vacuum generator 40, and the timer 52, as well as the cadencer 53 (or a microprocessor cumulating both these functions), which can be switched over (in the particular embodiment shown) so to actuate either of the adjustable pulsating vacuum lines A–B.

A subordinate switch 54 actuates the massage line through D. All timed operations are signalled by light indicators 55 and are controlled by the timer or the microprocessor and displayed, as regards the residual time to dispatch the step, by the integrator display 31 (see FIG. 3).

All controls and supervision instruments indicated in the diagrams are installed on one single front panel board 30 (see FIG. 3), together with the vacuum gauges 45 and 46 of the two steps. According to an embodiment of the present invention, each sitting of the treatment of the scalp comprises the following stages carried out in succession and in the following sequence:

First Stage

A warm solution is applied to the scalp for roughly 10 minutes which is made up of:
 1 liter of pure alcohol,
 100 gr. of rosemary,
 100 gr. of nettle,
 50 gr. of burdock,
 10 liters of warm distilled water, and
 100 gr. of precipitated sulphur.

The sulphur and the alcohol act as "vasodilators". The rosemary acts as "fixative" in the sense that it contributes to stabilize close to the hair bulbs the blood drawn up by the suction cups in the suction treatment in the following phase.

The nettle and the burdock are cell stimulants and contribute to the revitalization and growth of the hair.

This treatment has the object of warming the cells and preparing them for the physiotherapy treatment to follow.

Second Stage

In this stage, which is of a physiotherapy type, use is made of the vacuum generator provided with the connections D for frusto-conical sliding suction cups 1 and A and B for stationary suction cups 5. Each frusto-conical suction cup 1 has a single suction hole which creates a concentrate and passing suction action.

The frusto-conical suction cups 1 are made to run over the skin thus creating a momentary suction action. Wide diameter suction cups 5 create a localized "prolonged" suction action, that is suction cups which remain attached to one point on the skin for a certain interval of time.

The suction actions of the large diameter suction cups 5 are of the "pulsating" type, that is the degree of vacuum is varied cyclically. Flexible connections 28 join the suction cups 1 and 5 to the respective connections A and B or D of the device 30.

The suction cups are attached and detached easily from the respective connection by means of bayonet connections, or of another type, not indicated on the drawings.

Figure 6:
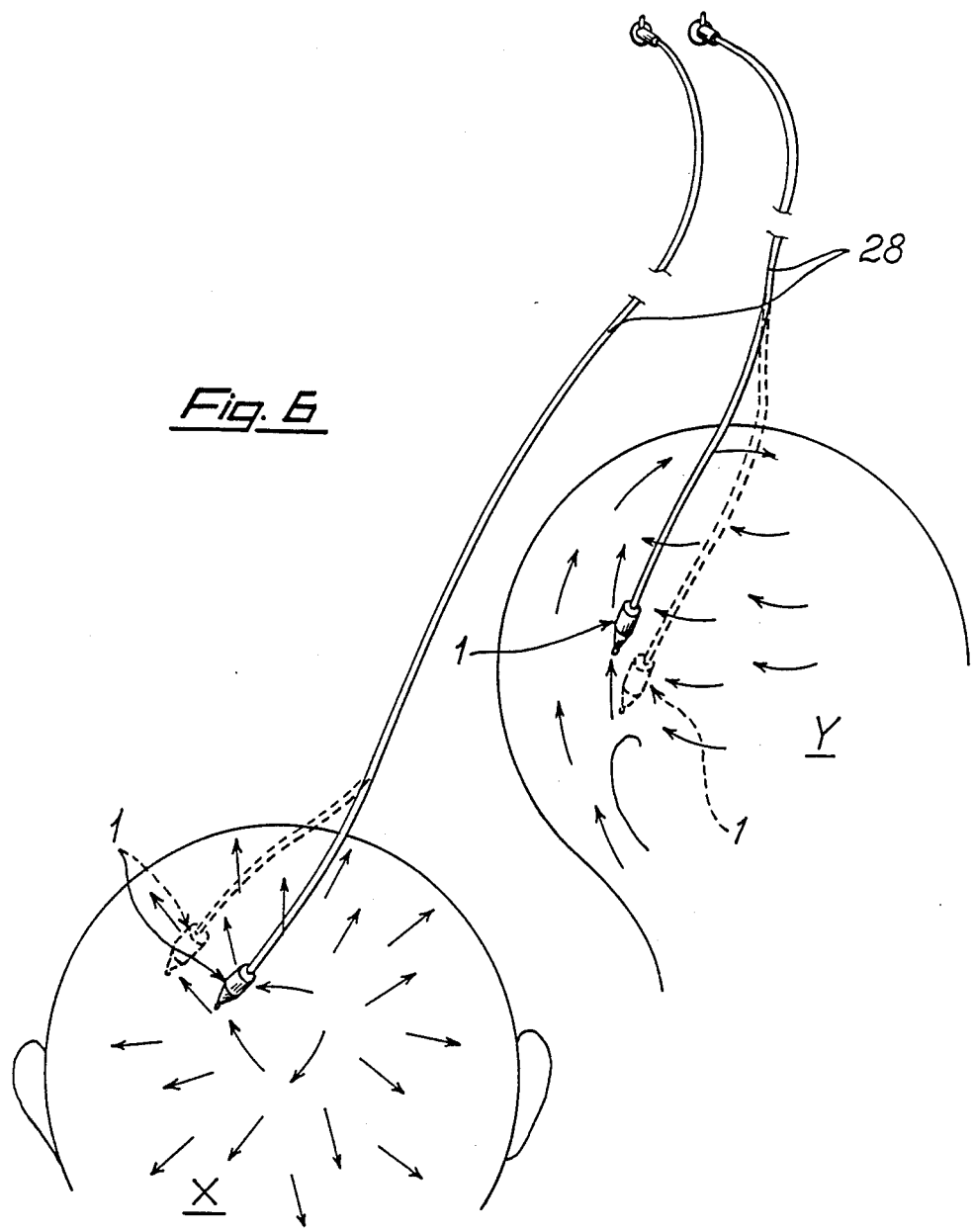
FIG. 6 illustrates the use of frusto-conical suction cups for the treatment of the scalps of two patients at the same time.
Figure 8:
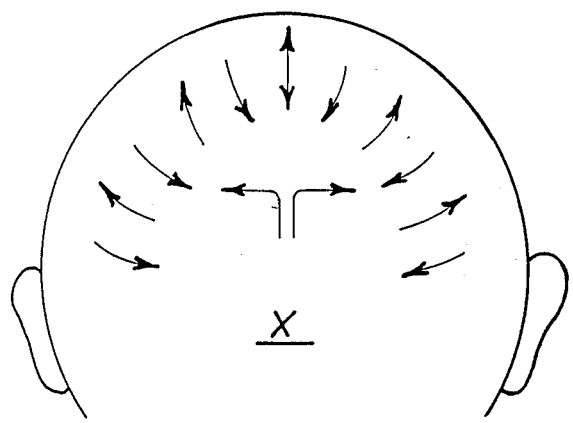
FIG. 8 shows the movements of the frusto-conical suction cups used on the front part of the head of the patient.

This second stage is done in two phases: in the first phase the "sliding" suction frusto-conical cups 1 are made to run over the scalp, for example on the heads X (seen from the side) and Y (seen from the back) of two patients; (FIGS. 8 and 9) in FIG. 6 the arrows indicate the route of the suction cups at each area. The suction cups 1 indicated by a dotted line in FIG. 6 are at the beginning of the route and those indicated by a full line are at the end of the same. The distance between the beginning and the end of the route is about 2–6 cm.

In this first phase, the suction is discontinuous or at intervals. When one area is covered, one passes to the following adjacent area in a sort of zig-zag.

Each area requires a treatment of more or less 5 minutes and the entire sitting is more or less one hour.

In the second phase, likewise of roughly 1 hour, the "fixed-pulsating" suction cups 5 are used which are applied (FIG. 7) to the areas of the head of patient X who has already undergone the first phase of treatment.

Tests made by Applicant proved that the concentrated passing suction action must be carried out before the localized prolonged suction action.

The average time of application, for each area, is roughly 10 minutes. In this second phase, the suction is cyclic. During this phase the device, correctly regulated, cyclically determines a phase of maximum vacuum value of the duration of roughly 12–14 seconds and then a phase with a lower value of 7–8 seconds. The number of the cyclic evolutions is 3–5 for min.

After this treatment with the pulsating suction cups, the treated scalp may be treated with warm packs of the solution used in the first phase, using the infrared rays for heating. Ultaviolet rays may be optionally used for a progressive time of from 3–15 minutes.

The total duration of each sitting is roughly 2.5 hours and is given once a week.

Figure 9:
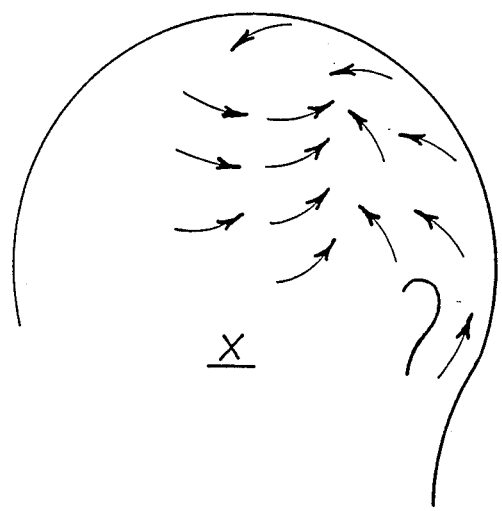
FIG. 9 shows the movements of the frusto-conical suction cups used on the left side of the head of the patient.

Tests made by the Applicant on many patients have shown interruption in the fall of hair right from the first few weeks of the treatment. After roughly ten weeks a beginning of regrowth was found. Obviously the treatment described can be given on all parts of the head and therefore even on the front of the head X (FIG. 8) or on the opposite side (FIG. 9). The arrows show the movements preferable for the "sliding" application. Naturally treatment can be given with the device to several patients at the same time. Thus, for example, FIG. 6 shows the treatment with sliding suction cups 1 on both the back part of the head of patient X and on the right side of patient Y. The suction cups 5 can be applied to a third patient who has finished the treatment with the sliding suction cups. Suction actions of various types obtained with the frusto-conical and the large diameter suction cups create on the various areas of the scalp effects similar to massage but much more intense and with the difference that they work at right angles to the skin and not predominantly parallel as with the massage itself.

The suction action also causes a temporary dilatation of the capillaries and the vessels greatly facilitating the flow of blood and lymph. The pulsating suction action from two or more different vacuum values determines, owing to a natural internal reaction, a stimulation of the circulation from the inside towards the outside and from the outside towards the inside.

The result is that the treatment subject of this invention increases the circulation by drawing from the lower levels the blood and the nutrients, while the toxic waste is eliminated and the cellular metabolism is greatly increased.

The method of the present invention was applied on about 3,000 patients suffering from a generic (hormonal, seborric or hereditary) baldness or from a stress deriving baldness (telogen effluvium). The results obtained are listed in the following tablets; the patients are subdivided according to the starting baldness stages, as classified by Arthur Rook-Rodney Dawber-"Malattie dei capelli e del cuoio capelluto" LE-Capozzi Editore, pages 108–110, and the age.

The results were determined by the visual and trichogram analysis of the hair before and after the treatment. In the tables, the result is given by the percentage of hair growth.

TABLE 1

Treatment carried out on patients suffering from a generic baldness

BALDNESS STAGING

| STAGE | AGE | MAN | WOMAN | RESULT |
|---|---|---|---|---|
| IV | 18–25 | 85 | 13 | 90% |
| IV | 26–33 | 80 | 20 | 90% |
| IV | 34–41 | 48 | 18 | 90% |
| IV | 42–49 | 16 | 14 | 90% |
| IV | +50 | 14 | 8 | 90% |
| V | 18–25 | 87 | 12 | 90% |
| V | 26–32 | 205 | 30 | 90% |
| V | 33–41 | 180 | 35 | 90% |
| V | 42–49 | 106 | 12 | 90% |
| V | +50 | 43 | 10 | 85% |
| VI | 18–25 | 20 | 8 | 90% |
| VI | 26–32 | 100 | 18 | 90% |
| VI | 33–41 | 146 | 23 | 85% |
| VI | 42–49 | 132 | 25 | 80% |
| VI | +50 | 45 | 22 | 75% |
| VII | 18–25 | 5 | — | 90% |
| VII | 26–32 | 28 | 2 | 85% |
| VII | 33–41 | 42 | 11 | 85% |
| VII | 42–49 | 65 | 13 | 75% |
| VII | +50 | 40 | 18 | 65% |
| VIII | 18–25 | 9 | — | 80% |
| VIII | 26–33 | 22 | — | 75% |
| VIII | 34–41 | 38 | 2 | 70% |
| VIII | 42–49 | 60 | 4 | 65% |
| VIII | +50 | 43 | 7 | 60% |

TABLE II

Treatment carried out on patients suffering from telogen effluvium.

TELOGEN EFFLUVIUM STAGING

| STAGE | AGE | MAN | WOMAN | RESULT |
|---|---|---|---|---|
| 1 | 18–25 | 4 | 37 | 90% |
| 1 | 26–33 | 2 | 32 | 90% |
| 1 | 34–41 | 5 | 27 | 90% |
| 1 | 42–49 | — | 16 | 85% |
| 1 | +50 | — | 18 | 85% |
| 2 | 18–25 | 3 | 12 | 90% |
| 2 | 26–33 | 7 | 31 | 90% |
| 2 | 34–41 | 3 | 13 | 85% |
| 2 | 42–49 | — | 24 | 75% |
| 2 | +50 | — | 8 | 75% |
| 3 | 18–25 | 8 | 13 | 70% |
| 3 | 26–33 | 3 | 28 | 70% |
| 3 | 34–41 | 4 | 22 | 65% |
| 3 | 42–49 | — | 25 | 60% |
| 3 | +50 | — | 11 | 60% |

The following experiments demonstrate that it is necessary to carry out the treatment first with the sliding suction cups and then with the pulsating stationary suction cups of larger diameter and that the opposite sequence would not be satisfactory.

Further, it is necessary to apply both types of suction in sequence. Fifteen test subjects having varying degrees of hair loss and of varying ages were selected and status of the test subjects is reported in the attached table. The test subjects were divided into three groups (Group A, Group B and Group C). Each group of five test subjects was subjected to the following treatments:

Group A

Each test subject was subjected to a massage treatment with a warm solution, applied to the scalp for about 10 minutes, consisting of:
1 l. of pure alcohol,
100 g. of rosemary,
100 g. of nettle,
50 g. of burdock,
10 l. of warm distilled water, and
100 g. of precipitated sulphur.

Each test subject, treated with the warm solution, was subjected to a sliding suction action by means of the frusto-conical suction means having a diameter of 15 mm, connected to a vacuum generator. The vacuum value was 0.5 kg/cm$^2$. The area involved in each treatment was about 4 cm$^2$ and the treatment was carried out in a zig-zag fashion by sliding the suction means over the skin of the scalp.

The treatment time for each area was about 5 minutes and the entire setting about 1 hour.

The massage with the warm solution followed by the treatment with the cigar-shaped suction cups was carried out once a week. The results obtained after 10 treatments for each subject are listed in the attached table.

Group B

Each test subject was treated with the same warm solution of Group A. The massage treatment and the duration time were the same as Group A. Each test subject was then subjected to a fixed and pulsating suction action by the large diameter suction cups having an inner volume of 27 cm$^3$. The treatment time for each area was about 10 minutes and during this time the large diameter suction cup was maintained fixed on the same area and a maximum vacuum value of 0.6 kg/cm$^2$ for the duration of 12–14 seconds followed by a low vacuum value of 0.2 kg/cm$^2$ for 7–8 seconds was cyclically applied. The entire setting was about 1 hour. The massage with the warm solution followed by the treatment with the large diameter suction cups was carried out one a week. The results obtained after 10 treatments for each subject are listed in the attached table.

Group C

Each test subject of this group was first treated with the same warm solution used for Group A.

The massage treatment and the duration time were the same as Group A.

Each treated test subject was first subjected to sliding suction actions by the cigar-shaped suction cups (1) having a diameter of 15 mm and connected to a vacuum generator. The vacuum value was 0.5 kg/cm$^2$. The area involved in each treatment was about 4 cm$^2$ and the treatment was carried out in zig-zag fashion, as illustrated in FIG. 6, by sliding the suction cups over the skin of the scalp. The treatment time for each area was about 5 minutes.

Figure 7:
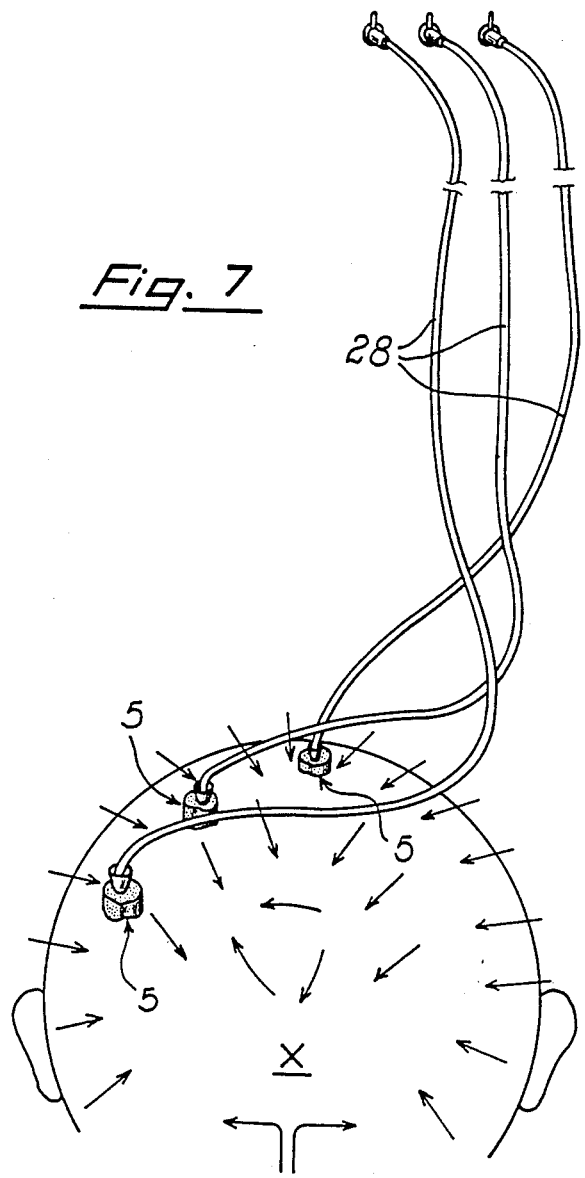
FIG. 7 illustrates the use of suction cups for prolonged applications.

Each test subject was then subjected, at the same sitting, to fixed and pulsating suction actions by the large diameter suction cups (5) having an inner volume of 27 cm$^3$, as illustrated in FIG. 7. The treatment time for each area was about 10 minutes and during this time the larger diameter suction cup (5) was maintained fixed on the same area and a maximum vacuum value of 0.6 kg/cm for the duration of 12–14 seconds followed by a low vacuum value of 0.2 kg/cm$^2$ for 7–8 seconds was cyclically applied.

The entire setting was 2 hours.

The massage with the warm solution followed by the treatment first with cigar-shaped suction cups and then with large diameter suction cups was carried out once a week.

The results obtained after 10 treatments for each subject are listed in the enclosed table.

TABLE

| SUBJECT | AGE years | STATE BEFORE TREATMENTS | CONDITION | TRICHOGRAM | RESULTS AFTER 10 SETTINGS | STAGE | TRICHOGRAM |
|---|---|---|---|---|---|---|---|
| | | | GROUP A | | | | |
| 1 | 32 MAN | Progressive hair loss since the age of 25 years Thinning out of the forehead temporal areas Denudation of the hind vertex with only some sparse hair. | Androgenetic Alopecia of VI stage Familiarity positive. Presence of sebum | Anagen: 40% Telogen: 60% | No improvement Continuous hair loss. | VI | Anagen: 40% Telogen: 60% |
| 2 | 36 MAN | Progressive hair loss since the age of 24 years Intensive denudation in the front temporal area with expansion to the back vertex Intensive denudation in the back vertex | Androgenetic Alopecia of VIII stage Hair loss after a surgical operation | Anagen: 50% Telogen: 50% | No improvement Continuous hair loss. | VIII | Anagen: 50% Telogen: 50% |
| 3 | 28 MAN | Bi-temporal hair recession with a perceptive thinning in the back vertex. Front-temporal hair recession | Androgenetic Alopecia of V stage Progressive hair loss after military service | Anagen: 45% Telogen: 55% | Continuous progressive hair loss. | V | Anagen: 40% Telogen: 60% |
| 4 | 25 WOMAN | Hair recession along the bi-temporal edge and hair loss in the temporal front part. | Telogen effluvium of 2 stage Hair loss after depressing syndrome | Anagen: 60% Telogen: 40% | Continuous hair loss. | 2 | Anagen: 50% Telogen: 50% |
| 5 | 23 WOMAN | Bi-temporal hair recession Increased hair loss in the area joining the vertices. | Androgenetic Alopecia of VI stage. Not-normal hormone analysis. Thin and depigmented hair | Anagen: 50% Telogen: 50% | Continuous hair loss. | VI | Anagen: 50% Telogen: 50% |
| | | | GROUP B | | | | |
| 1 | 39 MAN | Progressive hair loss since the age of 30 years. Bi-temporal hair recession Forehead-temporal hair loss | Androgenetic Alopecia of V stage. Sebum Dermatite Itch-burning | Anagen: 40% Telogen: 60% | No improvement Continuous hair loss. Irritation of the skin during the suctions. | VI | Anagen: 30% Telogen: 70% |
| 2 | 23 MAN | Hair loss since the age of 21 years Bi-temporal hair recession Hair loss in the vertex area. | Androgenetic Alopecia of IV-V stage. Light telogen effluvium in the parietal parts. Sideropenic anemy. | Anagen: 45% Telogen: 55% | No improvement Irritation of the skin during the suction. | V | Anagen: 45% Telogen: 55% |
| 3 | 28 MAN | Front-temporal hair recession Bi-temporal hair recession with a perceptive thinning in the back vertex | Androgenetic Alopecia of VI stage. Hair loss after a serious illness and use of drugs. | Anagen: 30% Telogen: 70% | No improvement Irritation of the skin during the suction. | VII | Anagen: 30% Telogen: 70% |
| 4 | 35 WOMAN | Progressive hair loss since the age of 22 years Androgenetic Alopecy at II stage, typical of the women subject. | Androgenetic Alopecia of V stage. Hormonal analysis: LM values lower than the normal ones. | Anagen: 50% Telogen: 50% | No improvement Some irritations of the skin during the applications. | V | Anagen: 50% Telogen: 50% |
| 5 | 45 MAN | Progressive hair loss since the age of 35 years. Bi-temporal hair recession Increased hair loss and thinning in the areas joining the back vertex. | Androgenetic Alopecia of VII stage. High sebum. Pitiriasic desquamation. | Anagen: 30% Telogen: 70% | No improvement Irritation of the skin | VII-VIII | Anagen: 30% Telogen: 70% |
| | | | GROUP C | | | | |
| 1 | 25 MAN | Progressive hair loss since the age of 20 years Increased hair loss on all the area of the scalp and particularly in the areas near the anterior and back vertices | Androgenetic Alopecia of VI stage. Seborric dermatite. Itch. Progressive hair loss after military service | Anagen: 40% Telogen: 60% | Stop of the hair falling Starting of the recovery | V | Anagen: 65% Telogen: 35% |
| 2 | 22 MAN | Progressive hair loss since the age of 18 years Bi-temporal hair recession since the age of 16 years Thinning in the areas joining the back vertices | Androgenetic Alopecia of V stage worse by Telon Effluvium due to the work stress | Anagen: 45% Telogen: 55% | Stop of the hair loss Starting of the growth of the hair in the bi-temporal area | IV | Anagen: 70% Telogen: 30% |
| 3 | 23 WOMAN | Increased hair loss since the age of 21 years Bi-temporal hair recession Increased hair loss in the area joining the vertices | Telogen Effluvium of 3 stage. Depressing syndrome after pregnancy | Anagen: 50% Telogen: 50% | Stop of the loss 50% recovery in the temporal areas | 2 | Anagen: 70% Telogen: 30% |
| 4 | 40 MAN | Progressive hair loss since the age of 30 years Bi-temporal hair recession | Androgenetic Alopecia of VII stage and slight Telogen Efflu- | Anagen: 35% Telogen: 65% | Stop of the loss | VII-VI | Anagen: 60% Telogen: 40% |

TABLE-continued

| SUBJECT | AGE years | STATE BEFORE TREATMENTS | CONDITION | TRICHOGRAM | RESULTS AFTER 10 SETTINGS | STAGE | TRICHOGRAM |
|---|---|---|---|---|---|---|---|
| | | Thinning in the areas joining the back vertex | vium of 1 stage due to the depressing syndrome after divorces Pitiriasic desquamation. Sebum | | | | |
| 5 | 35 WOMAN | Progressive hair loss since the age of 22 years | Androgenetic Alopecia of VI stage and Telogen Effluvium of 2 stage | Anagen: 40% Telogen: 60% | | VI-1 | Anagen: 55% Telogen: 45% |

The reason for using the two steps in the sequence mentioned herein-above is that if the pulsating suction were applied first with the large suction means, the skin would be raised too much and massage could not be carried out because it would cause too much irritation. Further, it is important when the cyclic pulsating suction is applied to have the inner bead in the suction cups as shown in FIGS. 2A and 2B, and that the material be rigid, otherwise if a deformable material were used and without the inner bead, the skin would be raised. The treatment is carried out for a period of 10 weeks with a two-hour duration each week. The first treatment with the sliding frustoconical suction cups lasts about one hour and is carried out about 1.5 minutes per each area of the scalp. The second treatment with the pulsating cyclic suction cups is also carried out for one hour applying the suction cups for about 10 minutes for each section of the scalp. In the treatment with the pulsating suction cups, the vacuum varies from a minimum of 0.1–0.75 kg/cm$^2$ to a maximum of 2–15 kg/cm$^2$ This corresponds to a minimum of 2–3 cycles per minute.

What is claimed is:

1. An apparatus for trichologic treatment of the scalp under variable partial vacuum which comprises:
    (a) a plurality of sliding suction means each having an elongated shape of diameter from 10 to 20 mm, a wall thickness of 2–4 mm and a rounded edge at an end intended to contact the scalp thus forming a frustoconical cup;
    (b) a plurality of cup-shaped stationary suction means (5) capable of creating a pulsating vacuum, each stationary suction means having a diameter between 25 and 50 mm, a wall thickness of 4 mm, a rounded edge and a bead (7) along the inner circumference; and
    (c) a vacuum generator (40) having two pneumatic circuits (41, 42), one circuit being connected to the sliding suction means for creating a vacuum between 0.3 and 0.75 kg/cm$^2$ under a thrust of 2–15 kg, the other circuit being connected to the stationary suction means for creating a pulsating vacuum varying alternately between 0.1 and 0.75 kg/cm$^2$ under a thrust of 2–15 kg;
    (d) regulating means (43, 44) with vacuum gauges (45, 46) connected with each pneumatic circuit for regulating the source intensity of each circuit;
    (e) regulating means (47) connected to the circuit of the stationary suction means for regulating the pulsating action intensity of vacuum and the period of time of action of said stationary suction means, and a timer for applying first said sliding suction means for a predetermined period of time and then said stationary suction means for a predetermined period of time.

2. An apparatus according to claim 1 wherein said frustoconical cups and the stationary suction means are made of a material which does not conduct heat.

3. The apparatus according to claim 2 wherein said material is a polyamide.

4. The apparatus according to claim 3 wherein the polyamide is nylon.

5. The apparatus according to claim 1 wherein the diameter of the sliding suction means is 15 mm and the diameter of the stationary suction means is 40 mm.

6. A method of activating the circulation of blood and lymph and nourishing the hair bulbs on a human scalp which consists of:
    (a) sliding a first suction means in a zig-zag fashion across the scalp to apply suction at a right angle to the scalp and then
    (b) maintaining a second suction means stationary at selected locations on the scalp and simultaneously applying a pulsating suction at a right angle to the scalp, the said pulsating suction being between a maximum value of vacuum for 12 seconds–14 seconds followed by a minimum value of vacuum for 7 seconds–8 seconds.

7. The method according to claim 6 wherein a warm solution containing vasodilating, stimulating and fixative agents is applied to the scalp prior to step (a).

8. The method according to claim 7 wherein said solution is an alcoholic solution containing 100 g. of sulfur, 100 g. of rosemary, 100 g. of nettle, 50 g. of burdock, 10 liters of water and 1 liter of alcohol.

9. The method according to claim 7 wherein after step (b), a step (c) is carried out in which said application of said warm solution is repeated.

10. The method according to claim 9 wherein after step (c), ultraviolet irradiation is applied.

11. The method according to claim 6 wherein said first suction means is a sliding frustoconical suction means, sliding over the skin of the scalp, and the second suction means is a stationary cup-shaped suction means.

12. The method according to claim 6 wherein the treatment in step (a) is carried out in each area of the scalp for about 5 minutes; in step (b) the stationary pulsating and suction is applied for each area of the scalp, for about 10 minutes.

13. The method according to claim 6 wherein the vacuum applied to the sliding suction means is between 0.3 and 0.75 kg/cm$^2$, and the vacuum applied to the stationary suction means varies from 0.1 to 0.75 kg/cm$^2$, maintaining a thrust variable from 2 to 15 kg.

14. The method according to claim 9 wherein after treatment with said warm solution, infrared radiation is applied.

* * * * *

UNITED STATES PATENT AND TRADEMARK OFFICE
CERTIFICATE OF CORRECTION

PATENT NO. : 4,836,192

DATED : June 6, 1989

INVENTOR(S) : Mariarosa Abbate

It is certified that error appears in the above-identified patent and that said Letters Patent is hereby corrected as shown below:

On the title page:

--Mariarosa Abbate, Giulio Corti, part interest--

Signed and Sealed this

Twenty-second Day of May, 1990

*Attest:*

HARRY F. MANBECK, JR.

*Attesting Officer*      *Commissioner of Patents and Trademarks*